United States Patent [19]

Imig et al.

[11] 4,346,754
[45] Aug. 31, 1982

[54] HEATING AND COOLING SYSTEM

[75] Inventors: Leland A. Imig, Goehner, Nebr.; Mickey R. Gardner, Gloucester Point, Va.

[73] Assignee: The United States of America as represented by the Administrator of the National Aeronautics and Space Administration, Washington, D.C.

[21] Appl. No.: 145,208

[22] Filed: Apr. 30, 1980

[51] Int. Cl.³ .............................................. F25B 29/00
[52] U.S. Cl. ........................................ 374/46; 165/27; 165/61; 165/80 E; 165/12; 62/62; 62/514 R
[58] Field of Search .................... 165/11 R, 12, 27, 61, 165/63, 64, 80 E; 62/62, 514 R, 78; 73/15 R, 15.4

[56] References Cited

U.S. PATENT DOCUMENTS

| | | | |
|---|---|---|---|
| 3,143,167 | 8/1964 | Vieth | 165/64 |
| 3,406,742 | 10/1968 | Naumann et al. | 165/12 |
| 3,453,863 | 7/1969 | Scott | 73/15 R |
| 3,599,475 | 8/1971 | Dubouch et al. | 73/15 R |
| 4,107,937 | 8/1978 | Chmiel | 62/64 |
| 4,117,881 | 10/1978 | Williams et al. | 165/2 |
| 4,134,447 | 1/1979 | Jennings et al. | 165/30 |

FOREIGN PATENT DOCUMENTS

| | | | |
|---|---|---|---|
| 2432734 | 4/1980 | France | 73/15 R |
| 435481 | 7/1975 | U.S.S.R. | 73/15 R |
| 533850 | 11/1976 | U.S.S.R. | 73/15 R |
| 563603 | 6/1977 | U.S.S.R. | 73/15 R |

Primary Examiner—Albert W. Davis
Assistant Examiner—Margaret A. Focarino
Attorney, Agent, or Firm—Howard J. Osborn; John R. Manning; William H. King

[57] ABSTRACT

A heating and cooling apparatus capable of cyclic heating and cooling of a test specimen undergoing fatigue testing. Cryogenic fluid is passed through a block 10 clamped to the specimen 11 to cool the block and the specimen. Heating cartridges 13 penetrate the block 10 to heat the block and the specimen 11 to very hot temperatures. Control apparatus 36 and 46 is provided to alternately activate the cooling and heating modes to effect cyclic heating and cooling between very hot and very cold temperatures. The block 10 is constructed of minimal mass to facilitate the rapid temperature change thereof.

9 Claims, 4 Drawing Figures

HEATING AND COOLING SYSTEM

ORIGIN OF THE INVENTION

The invention described herein was made by employees of the U.S. Government and may be manufactured and used by or for the Government for governmental purposes without the payment of any royalites thereon or therefor.

BACKGROUND OF THE INVENTION

The present invention relates to material fatigue testing and particularly to an apparatus for maintaining a test specimen at a control temperature and for cyclically inducing a range of temperatures between cryogenic and elevated.

Spacecraft endure a wide range of temperatures during space flights. The portion of the spacecraft exposed to the intense direct rays of the sun experience elevated temperatures while the portion of the spacecraft shaded from the sun experience relatively lower temperatures. Moreover, the spacecraft as a whole experiences low temperatures during travel through the shadow of a planet or other heavenly body. The temperatures vary from cryogenic, hundreds of degrees below 0° centigrade, to elevated, hundreds of degrees above 0° centigrade. Furthermore, the temperature of a particular spacecraft structural component may experience a wide range of temperatures in a short period of time during rotation of the spacecraft, in that the particular component is alternately exposed to the sun's rays and shaded therefrom.

In the testing of structural components of spacecraft it is desirable to simulate as closely as possible the pertinent environmental conditions the structure will experience in space. Accordingly, in the fatigue testing of structural components of spacecraft it is desirable to expose the structure to extreme high and low temperatures while maintaining a load on the test specimen. Relatively massive commercial systems are available in the prior art either as heat sources or as cryogenic sources but none include cyclic temperature capabilities into the cryogenic temperature range. In some known systems test specimens are alternately transported between a cryogenic chamber and a hot chamber. However, these systems are unacceptable for tests in which the specimen position must remain fixed as in a testing machine.

The massive commercial systems of the prior art are incompatible with the fatigue testing machine designed to test small samples. Furthermore, they require large amounts of electricity for heating, large amounts of cryogenic material for cooling, and do not provide cyclic temperature capability. The systems which transport this space specimen between hot and cold chambers are inherently incompatible with the stationary configuration of a fatigue testing machine.

The present invention alleviates to a great extent the short comings of the prior art. In the present invention the same block having a small mass is used to transfer both elevated and cryogenic temperatures to the test sample. The block is clamped to the test specimen during fatigue testing. Liquid nitrogen is directed through the block for cooling it to cryogenic temperatures.

Heating cartridges accommodated by apertures in the block, are provided for heating the block to elevated temperatures. A thermocouple probe penetrates the block to monitor the temperature of the test specimen. Control devices are provided to supply liquid nitrogen through the block and for power to the heating cartridges in a manner to maintain a preselected temperature. Cyclic operation between elevated and cryogenic temperatures with hot and cold cycles of unequal lengths, and at arbitrary times is possible by utilizing a timing device to alternate between heating and cooling. The small mass of the block is the key feature of the invention because its temperature can be changed rapidly allowing quick heating and cooling of the test specimen.

An object of the invention is to provide an apparatus for heating and cooling a fatigue test specimen.

It is another object of the invention to provide a heating and cooling apparatus having a minimal mass to allow quick cooling and heating thereof.

A further object of the invention is a heating and cooling apparatus having the foregoing advantages and which is capable of cyclic operation between cryogenic and very hot temperature.

Another object of the invention is a heating and cooling apparatus having the foregoing advantages which can be easily custom made to fit fatigue test samples connected in place to a testing machine.

A further object of the invention is a heating and cooling apparatus having the foregoing advantages which is inexpensive and uses small amounts of energy to heat, and cryogenic materials to cool.

Other objects and advantages of the present invention will be readily apparent from the following description and drawings which illustrate the preferred embodiment of the invention.

SUMMARY OF THE INVENTION

The present invention involves a heating and cooling block being of minimum mass to enable rapid cooling and heating thereof. Cooling means are provided for cooling the block to cryogenic temperature and heating means are provided for heating the block to elevated temperature. Control means are provided for alternately activating the heating means and the cooling means.

DETAILED DESCRIPTION OF THE PREFERRED EMBODIMENT

Figure 1:
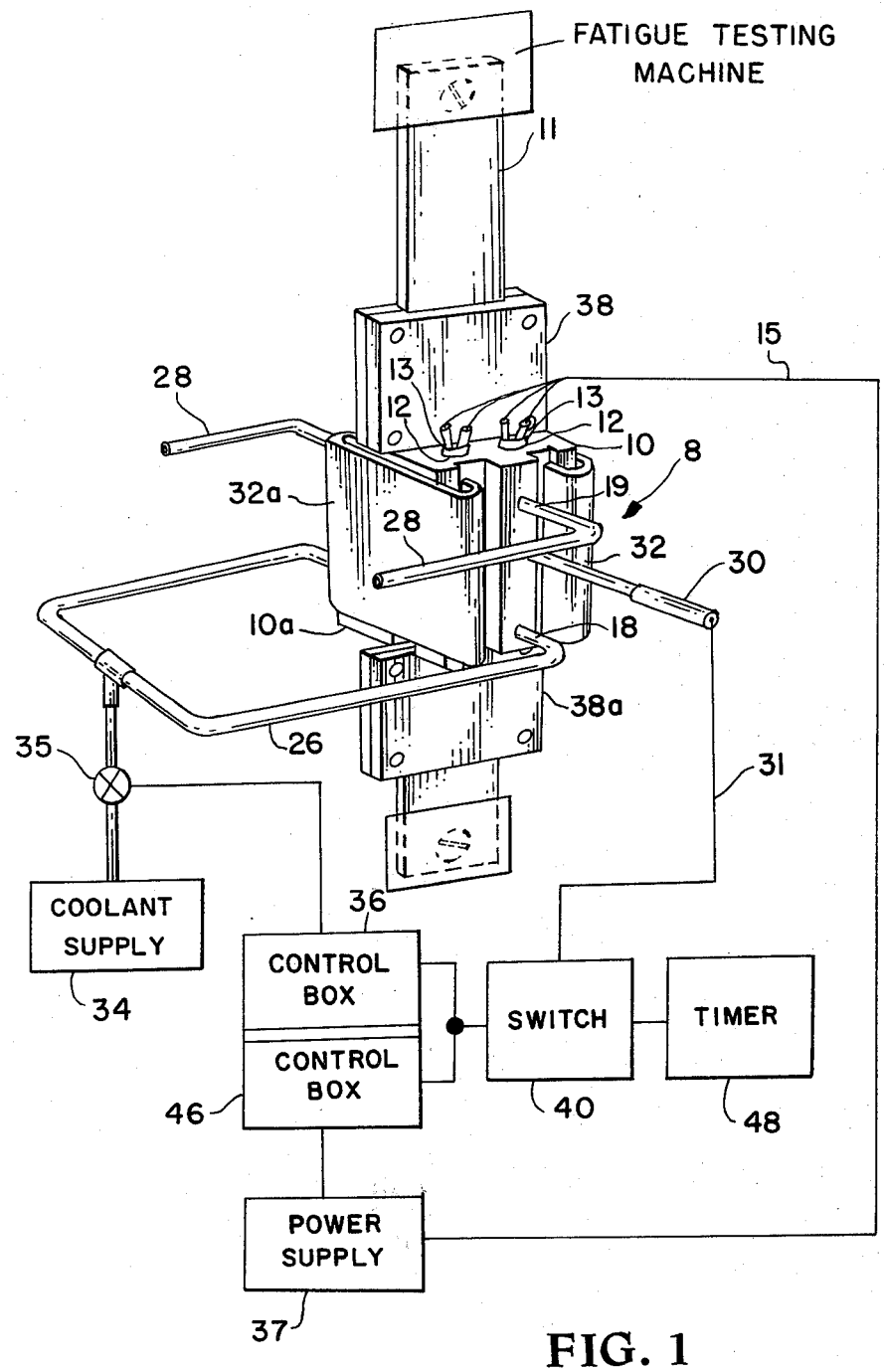
FIG. 1 is a perspective view of the preferred embodiment of a heating and cooling apparatus according to the present invention in place on a fatigue test specimen.

Referring now to FIG. 1 there is shown in perspective the preferred embodiment of the invention designated generally by the reference numeral 8. Flat elongated test specimen 11 is connected at both ends thereof to a fatigue test machine (not shown). Two identical blocks 10 and 10a are clamped to specimen 11 by clamps 32 and 32a. The clamps 32 and 32a are made of spring or resilient material and force the block 10 and 10a against the specimen. It is to be understood that other types of clamps might be utilized. Positioning plates 38 and 38a are affixed to specimen 11 above and below blocks 10 to preclude slippage of block 10 along specimen 11 and to keep the specimen from buckling.

Coolant flow is applied through the block by coolant supply 34 in fluid communication via inlet pipes 26 with chambers (see FIGS. 3-5) of block 10. The coolant of the preferred embodiment is cryogenic, typically liquid nitrogen. Coolant is exhausted as a vapor and exhaust pipes 28 provide fluid communication between block 10 and the atmosphere.

Solenoid operated valve 35 controls coolant flow through inlet pipe 26. Thermocouple probe 30 extends through block 10 to a position adjacent the specimen 11 to monitor temperature thereof.

A signal indicative of specimen 11 temperature is sent via wire 31 and switch 40 to solenoid control 36 whereby solenoid valve 35 is operated to maintain specimen 11 temperature at a desired set level. The solenoid control 36 and the solenoid valve 35 are of conventional design and available commercially.

Heating element cartridges 13 penetrate through block 10 and provide a source of heat thereto. Power supply 37 provides electrical power to cartridges 13 via wire 15. A signal indication of specimen 11 temperature is sent via wire 31 and switch 40 to power supply control 46 whereby the power supply is activated to maintain specimen 11 temperature at a desired set level.

Timing device 48 operates switch 40 to elect heating or cooling of the block for cyclic operation. The power supply 37, the switch 40, power supply controller 46, and timer are also of conventional design and are available from commercial suppliers. The details of the control structure and operation are considered known to one skilled in the art and need not be explained.

Figure 2:
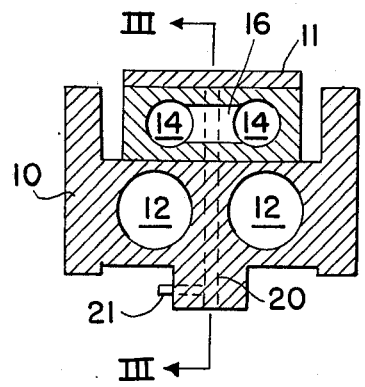
FIG. 2 is a sectional view of the block of the preferred embodiment of the heating and cooling apparatus according to the present invention.

Refer now to FIG. 2 there being shown a view of block 10 of the preferred embodiment. Heating element apertures 12 extend through block 10 and are sized to accept heating element cartridges 13 (see FIG. 1). Cylindrical coolant chambers 14 extend through block 10. Slots or conduits 16 and 17 establish fluid communication between chambers 14.

Figure 3:
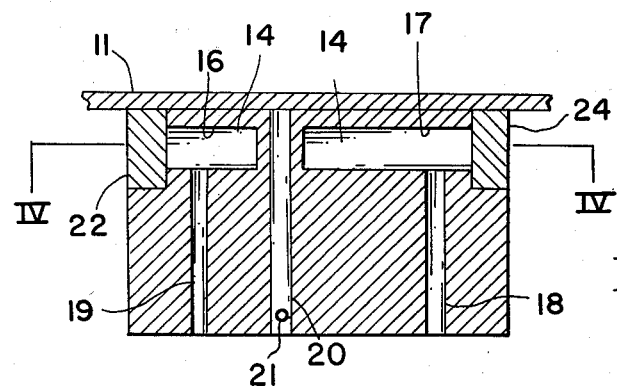
FIG. 3 is a cross-sectional view taken along line III—III of FIG. 2.

Refer now to FIG. 3. Thermocouple bore 20 extends through block 10 and is sized to accept thermocouple probe 30 (see FIG. 1). Securing screw 21 is provided to hold probe 30 in place. Inlet conduit 18 establishes fluid communication between inlet pipe 26 and slot 17; exit conduit 19 establishes fluid communication between slot 16 and exhaust pipe 28.

Caps 22 and 24 (shown in FIG. 4) are secured to block 10 by screws or other suitable means (not shown) to enclose chambers 14 and slots 16 and 17.

Figure 4:
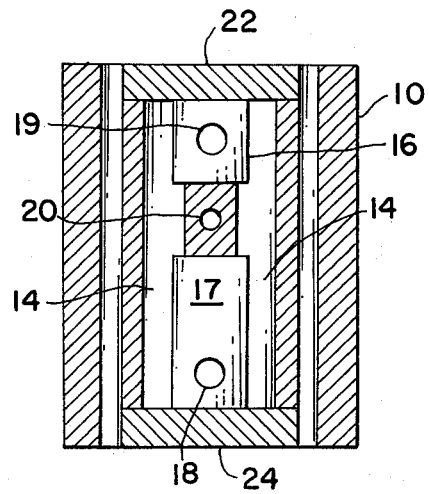
FIG. 4 is a cross-sectional view taken along line IV—IV of FIG. 3.

Turning to FIG. 4 another view is shown for clarity and to show cap 22 in position to establish a closed coolant passageway within block 10 consisting of slots 16, 17 and chambers 14.

In operation of the invention when used to maintain a constant cold temperature on the test specimen the coolant, typically liquid nitrogen (not shown), is introduced through coolant inlet pipe 26 by solenoid valve 35 from remote pressurized coolant source 34. Liquid nitrogen enters coolant containing chambers 14 and slots 16, and 17 of block 10 and absorb heat from the surrounding material of block 10 including heat conducted from specimen 11. Absorbed heat vaporizes the liquid nitrogen; the vapor then exhausts to the atmosphere through exhaust pipes 28. Liquid nitrogen continues to flow into block 10 until thermocouple feedback probe 30 (which is in contact with specimen 11) senses that the desired temperature has been achieved. Solenoid valve control 36 then closes solenoid valve 35 interrupting the flow of liquid nitrogen. When heat conducted from the surroundings tends to warm specimen 11; thermocouple probe 30 actuates solenoid valve control 36 to open solenoid valve 35 to allow nitrogen to flow, thus maintaining temperature within a narrow range.

The system functions similarly when used to maintain test specimens at constant elevated temperature. In this case, however, thermocouple probe 30 indicates the temperature of the specimen to control 46 which controls electrical power to heating cartridges 13.

The system operates alternately as a heater or cooler, in the ways described above, by introducing a device to alternately power liquid nitrogen controller 36 or elevated temperature controller 46 according to the requirements of a particular testing program. The system has operated successfully in a test wherein heat (600° F.) and cold (−250° F.) were achieved alternately by a simple timing device 48 which provides power alternately to the controllers 36 and 46. Cyclic operation between elevated and cryogenic temperatures with hot and cold cycles of unequal lengths and at arbitrary times depends on the characteristics of the device which activates controllers 36 and 46. If the device 48 which activates controllers 36 and 46 is the same device that sequences loads applied to specimen 11, the loading and temperature of specimen 11 can be either synchronized or phased at the discretion of the person conducting the tests. The latter mode of operation is the operation for which this system was devised. In actual tests it was found that a test specimen could be cooled from +600° F. to −250° F. in a time interval of 15 minutes and heated from a −250° F. to +600° F. in 9 minutes, enabling a cycle to be completed in 25 minutes. The small mass of block 10 is a key feature of the invention because its temperature can be changed relatively rapidly.

The above description and drawings are only illustrative of one embodiment which achieves the objects, features and advantages of the present invention, and it is not intended that the present invention be limited thereto. Any modification of the present invention which comes within the spirit and scope of the following claims shall be considered part of the present invention.

What is claimed as new and desired to be secured by Letters Patent of the United States is:

1. A device for heating and cooling a specimen undergoing fatigue testing comprising:
 a fatigue testing machine;
 a test specimen connected to said fatigue testing machine;
 block means having a small mass to enable rapid cooling and heating thereof;
 said block means being constructed and arranged to engage said test specimen;
 clamping means for securing said block means to said test specimen;
 cooling means for cooling said block means and test specimen to very cold temperatures;
 heating means for heating said block means and test specimen to very hot temperatures; and
 contol means for selectively activating said heating means and said cooling means to selectively heat and cool said test specimen.

2. A device as in claim 1 wherein said control means includes temperature sensing means for indicating test specimen temperatures;

cooling control means for selectively activating and deactivating said cooling means respondent to the temperature sensitive means to maintain a desired cold temperature; and heating control means for selectively activating and deactivating said heating means respondent to the temperature sensitive means to maintain the desired hot temperature.

3. A device as in claim 1 wherein said cooling means includes a supply of cryogenic fluid and conduit means extending from said supply of cryogenic fluid and through said block means.

4. A device as in claim 1 wherein said heating means includes at least one heating cartridge penetrating said block means.

5. A device as in claim 3 wherein said cooling control means includes a solenoid controlled valve positioned in said conduit means.

6. A device as in claim 2 wherein said control means further comprises a timing device for selectively activating said cooling means and said heating means to effect cyclic temperature of the test specimen between very hot and very cold temperatures at desired time intervals.

7. A device for heating and cooling a test specimen as in claim 1 wherein said block means is a pair of blocks; one of said blocks engaging one side of said test specimen and the other block engaging the other side of said test specimen substantially surrounding said test specimen to facilitate rapid heat transfer.

8. A device for heating and cooling a test specimen as in claim 1 including means for positioning said block means on said test specimen and preventing buckling thereof.

9. A device for heating and cooling a test specimen as in claim 1 wherein said block means includes multiple chambers and conduits to reduce the mass thereof and facilitate maximum flow of a heat transfer medium.

* * * * *